US012636072B2

(12) United States Patent
Baril et al.

(10) Patent No.:  US 12,636,072 B2
(45) **Date of Patent:  *May 26, 2026**

(54) SMOKE MITIGATION ASSEMBLY FOR BIPOLAR PENCIL

(71) Applicant: Covidien LP, Mansfield, MA (US)

(72) Inventors: Jacob C. Baril, Norwalk, CT (US); Matthew A. Dinino, Newington, CT (US); Saumya Banerjee, Southington, CT (US); Justin J. Thomas, New Haven, CT (US); Roy J. Pilletere, Middletown, CT (US)

(73) Assignee: Covidien LP, Mansfield, MA (US)

( * ) Notice: Subject to any disclaimer, the term of this patent is extended or adjusted under 35 U.S.C. 154(b) by 418 days.

This patent is subject to a terminal disclaimer.

(21) Appl. No.: 18/207,758

(22) Filed: Jun. 9, 2023

(65) Prior Publication Data

US 2023/0310064 A1     Oct. 5, 2023

Related U.S. Application Data

(63) Continuation of application No. 16/881,112, filed on May 22, 2020, now Pat. No. 11,684,413.

(51) Int. Cl.
A61B 18/14          (2006.01)
A61B 34/35          (2016.01)
(Continued)

(52) U.S. Cl.
CPC ............ *A61B 18/148* (2013.01); *A61B 34/35* (2016.02); *A61B 2017/00367* (2013.01);
(Continued)

(58) Field of Classification Search
CPC ........ A61B 18/148; A61B 2017/00367; A61B 2017/00371; A61B 2017/00411;
(Continued)

(56) References Cited

U.S. PATENT DOCUMENTS

| 2,022,065 A | 11/1935 | Wappler |
| 2,047,535 A | 7/1936 | Wappler |

(Continued)

FOREIGN PATENT DOCUMENTS

WO        2016025132 A1      2/2016

*Primary Examiner* — Eduardo C Robert
*Assistant Examiner* — Christina NegrelliRodriguez
(74) *Attorney, Agent, or Firm* — Carter, DeLuca & Farrell, LLP

(57) ABSTRACT

An electrosurgical pencil includes a housing having proximal and distal ends, the proximal end adapted to connect to an energy source and the distal end adapted to receive an end effector assembly therein, the end effector assembly defining a surface area along a length thereof. An activation switch is operably associated with the housing and is configured to deliver electrosurgical energy to the end effector assembly upon actuation thereof. An air control valve is operatively coupled to the activation switch and is configured to simultaneously deliver a gas from a gas source to the surface area around the end effector upon actuation of the activation switch. One or more vents are defined in the distal end of the housing and are configured to direct the gas towards the surface area of the end effector.

20 Claims, 7 Drawing Sheets

(51) Int. Cl.
    *A61B 17/00*        (2006.01)
    *A61B 18/00*        (2006.01)
    *A61B 18/12*        (2006.01)

(52) U.S. Cl.
    CPC .............. *A61B 2017/00734* (2013.01); *A61B 2018/00077* (2013.01); *A61B 2018/00589* (2013.01); *A61B 2018/00595* (2013.01); *A61B 2018/00601* (2013.01); *A61B 2018/00684* (2013.01); *A61B 2018/126* (2013.01); *A61B 2018/1412* (2013.01); *A61B 2218/008* (2013.01)

(58) Field of Classification Search
    CPC ........... A61B 2018/00077; A61B 2018/00589; A61B 2018/00595; A61B 2018/00601; A16B 2218/008
    USPC .......................................................... 606/41
    See application file for complete search history.

(56)                References Cited

U.S. PATENT DOCUMENTS

| | | | |
|---|---|---|---|
| 3,516,412 A | 6/1970 | Ackerman |
| 3,886,944 A | 6/1975 | Jamshidi |
| 4,161,950 A | 7/1979 | Doss et al. |
| 4,196,734 A | 4/1980 | Harris |
| 4,198,957 A | 4/1980 | Cage et al. |
| 4,485,810 A | 12/1984 | Beard |
| 4,534,347 A | 8/1985 | Taylor |
| 4,622,966 A | 11/1986 | Beard |
| 4,633,880 A | 1/1987 | Osypka et al. |
| 4,862,890 A | 9/1989 | Stasz et al. |
| 5,013,312 A | 5/1991 | Parins et al. |
| 5,085,659 A | 2/1992 | Rydell |
| 5,300,068 A | 4/1994 | Rosar et al. |
| 5,360,428 A | 11/1994 | Hutchinson, Jr. |
| 5,441,499 A | 8/1995 | Fritzsch |
| 5,531,744 A | 7/1996 | Nardella et al. |
| 5,536,267 A | 7/1996 | Edwards et al. |
| 5,599,295 A | 2/1997 | Rosen et al. |
| 5,599,346 A | 2/1997 | Edwards et al. |
| 5,611,798 A | 3/1997 | Eggers |
| 6,027,501 A | 2/2000 | Goble et al. |
| 6,217,528 B1 | 4/2001 | Koblish et al. |
| 6,494,881 B1 | 12/2002 | Bales et al. |
| 6,530,924 B1 | 3/2003 | Ellman et al. |
| 6,533,781 B2 | 3/2003 | Heim et al. |
| 6,752,767 B2 | 6/2004 | Turovskiy et al. |
| 7,033,354 B2 | 4/2006 | Keppel |
| 7,371,234 B2 | 5/2008 | Young |
| 7,399,299 B2 | 7/2008 | Daniel et al. |
| 7,419,488 B2 | 9/2008 | Ciarrocca et al. |
| 7,846,108 B2 | 12/2010 | Turovskiy et al. |
| 7,846,158 B2 | 12/2010 | Podhajsky |
| 8,137,345 B2 | 3/2012 | McNall, III et al. |
| 8,968,301 B2 | 3/2015 | Weber |
| 9,060,765 B2 | 6/2015 | Rencher et al. |
| 9,358,065 B2 | 6/2016 | Ladtkow et al. |
| 9,445,863 B2 | 9/2016 | Batchelor et al. |
| 9,775,665 B2 | 10/2017 | Ellman |
| 9,993,287 B2 | 6/2018 | Sartor et al. |
| 10,045,761 B2 | 8/2018 | Weber |
| 10,376,314 B2 | 8/2019 | van der Weide et al. |
| 10,433,898 B2 | 10/2019 | Borgmeier et al. |
| 10,433,899 B2 | 10/2019 | Borgmeier et al. |
| 10,531,917 B2 | 1/2020 | Johnson et al. |
| 11,399,888 B2 | 8/2022 | Baril et al. |
| 11,684,413 B2* | 6/2023 | Baril ................... A61B 18/148 606/41 |
| 2005/0070895 A1 | 3/2005 | Ryan et al. |
| 2005/0283149 A1 | 12/2005 | Thorne et al. |
| 2007/0078454 A1 | 4/2007 | McPherson |
| 2007/0118110 A1 | 5/2007 | Girard et al. |
| 2007/0149966 A1 | 6/2007 | Dahla et al. |
| 2007/0179494 A1 | 8/2007 | Faure |
| 2007/0219546 A1 | 9/2007 | Mody et al. |
| 2007/0260240 A1 | 11/2007 | Rusin |
| 2007/0265609 A1 | 11/2007 | Thapliyal et al. |
| 2008/0281323 A1 | 11/2008 | Burbank et al. |
| 2009/0306642 A1 | 12/2009 | Vankov |
| 2011/0306968 A1* | 12/2011 | Beckman ........... A61B 18/1482 606/41 |
| 2012/0116416 A1 | 5/2012 | Neff et al. |
| 2019/0083172 A1 | 3/2019 | Ladtkow et al. |

\* cited by examiner

SMOKE MITIGATION ASSEMBLY FOR BIPOLAR PENCIL

CROSS-REFERENCE TO RELATED APPLICATIONS

This application is a continuation of U.S. patent application Ser. No. 16/881,112, filed on May 22, 2020.

FIELD

The present disclosure relates generally to electrosurgical instruments and, more particularly, to an electrosurgical bipolar pencil configured for bipolar resection.

BACKGROUND

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical coagulation, electrosurgical sealing, electrosurgical cutting, and/or electrosurgical fulguration or, in some instances, an electrosurgical blend thereof.

In particular, electrosurgical fulguration includes the application of an electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments that have a handpiece which is attached to an active electrode and that is used to cauterize, coagulate and/or cut tissue. Typically, the electrosurgical pencil may be operated by a handswitch or a foot switch.

As mentioned above, the handpiece of the electrosurgical pencil is connected to a suitable electrosurgical energy source (e.g., generator) that produces the radio-frequency electrical energy necessary for the operation of the electrosurgical pencil. In general, when an operation is performed on a patient with an electrosurgical pencil in a monopolar mode, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

When an operation is performed on a patient with an electrosurgical pencil in a bipolar mode, the electrode face includes at least one pair of bipolar electrodes and electrical energy from the electrosurgical generator is conducted through tissue between the pair of bipolar electrodes.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. Surgeons typically follow preset control parameters and stay within known modes and power settings and electrosurgical pencils include simple and ergonomically friendly controls that are easily selected to regulate the various modes and power settings Electrosurgical instruments are typically configured such that power output can be adjusted without the surgeon having to turn his or her vision away from the operating site and toward the electrosurgical generator.

During use of a bipolar pencil, smoke may be generated while the tissue is being treated which, in some instances, may reduce visibility to the operative site. In these instances, the surgeon typically stops treatment and waits for the smoke to dissipate before continuing with treatment.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is an electrosurgical pencil having a housing including proximal and distal ends, the proximal end adapted to connect to an energy source and the distal end adapted to receive an end effector assembly therein, the end effector assembly defining a surface area along a length thereof. An activation switch is operably disposed on the housing and is configured to deliver electrosurgical energy to the end effector assembly upon actuation thereof. An air control valve is operatively coupled to the activation switch and is configured to simultaneously deliver a gas from a gas source to the surface area around the end effector assembly upon actuation of the activation switch. One or more vents are defined in the distal end of the housing and are configured to direct the gas towards the surface area of the end effector assembly.

In aspects according to the present disclosure, the gas is selected from the group consisting of carbon dioxide and air. In other aspects according to the present disclosure, the gas is delivered from the air control valve to the one or more vents in one or more corresponding tubes.

In aspects according to the present disclosure, the housing includes a plurality of vents defined about the distal end thereof that is configured to direct the gas to the surface area of the end effector assembly.

Provided in accordance with aspects of the present disclosure is an electrosurgical pencil having a housing including proximal and distal ends, the proximal end adapted to connect to an energy source and the distal end adapted to receive an end effector assembly therein, the end effector assembly defining a surface area along a length thereof. An activation switch is operably disposed on the housing and is configured to deliver electrosurgical energy to the end effector assembly upon actuation thereof. An air control valve is operatively coupled to the activation switch and is configured to deliver a gas from a gas source to the surface area around the end effector assembly upon actuation of the activation switch. The activation switch includes multiple stages for controlling both the electrosurgical energy and the delivery of gas to the end effector assembly. One or more vents are defined in the distal end of the housing and are configured to direct the gas towards the surface area of the end effector assembly.

In aspects according to the present disclosure, the activation switch includes two stages: a first activation stage that delivers electrosurgical energy to the end effector assembly; and a second stage that delivers both electrosurgical energy and gas to the end effector assembly. In other aspects according to the present disclosure, the transition from the first stage to the second stage of the activation switch is through the range of motion of the activation switch.

In aspects according to the present disclosure, the activation switch includes three stages: a first activation stage that delivers electrosurgical energy to the end effector assembly; a second stage that delivers both electrosurgical energy and gas to the end effector assembly; and a third stage that delivers the gas to the end effector assembly. In aspects according to the present disclosure, the transition from the first stage through the third stage of the activation switch is through the range of motion of the activation switch.

In aspects according to the present disclosure, one stage of the multiple stages of the activation switch includes delivering the gas to the end effector assembly at a first flow rate and a subsequent stage of the multiple stages of the activation switch includes delivering the gas to the end effector assembly at a different flow rate.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

4

Figure 1:
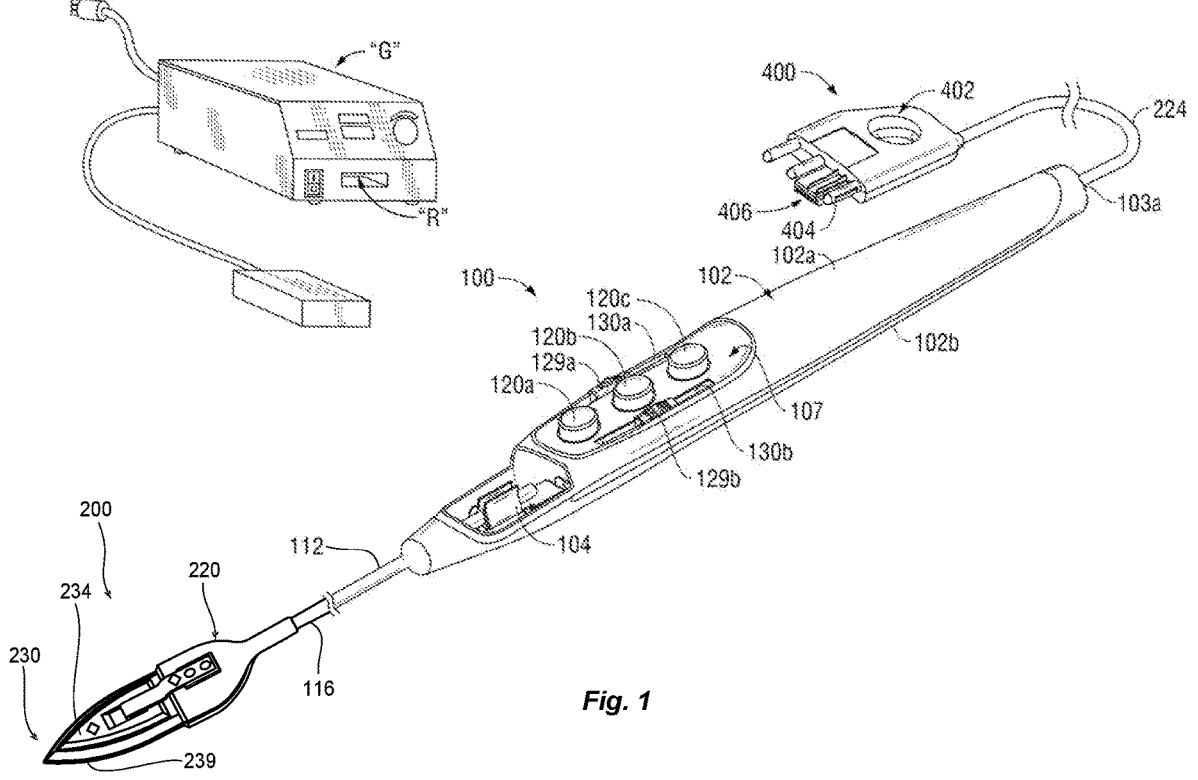
FIG. 1 is a perspective view of a commonly-owned electrosurgical system including an electrosurgical pencil including a housing having a shaft extending therefrom with an end effector attached to a distal end thereof, the end effector configured for bipolar resection in accordance with an embodiment of the present disclosure.
Figure 4:
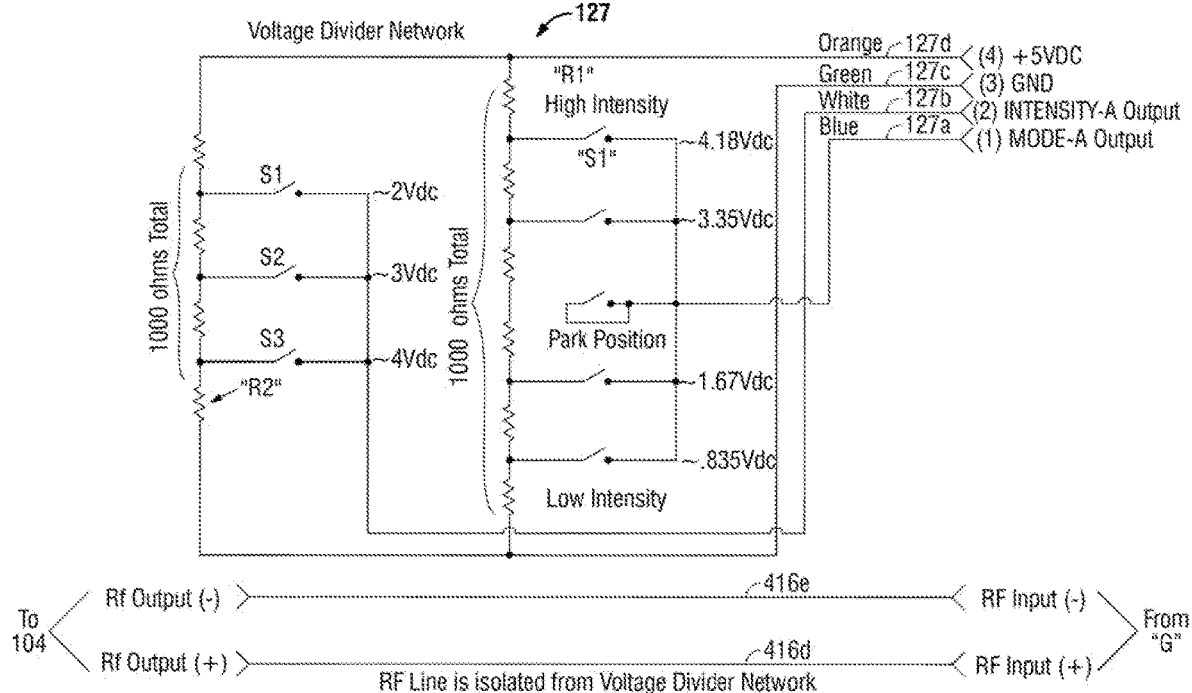
Figure 5A:
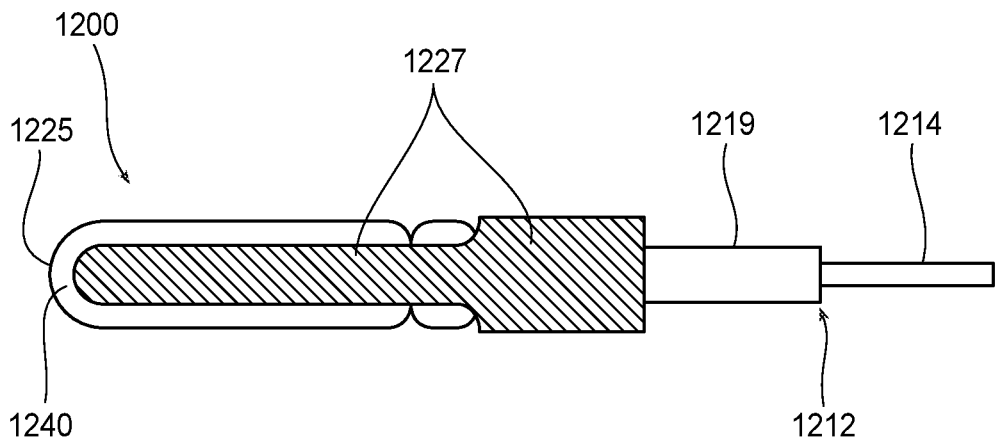
Figure 5B:
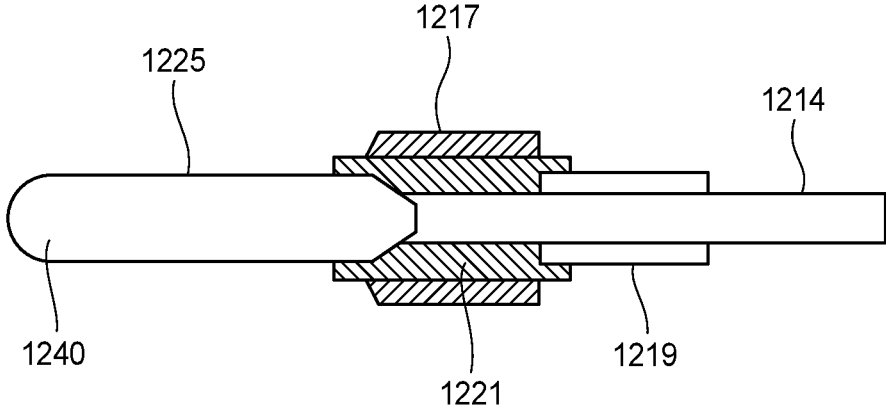
Figure 5C:
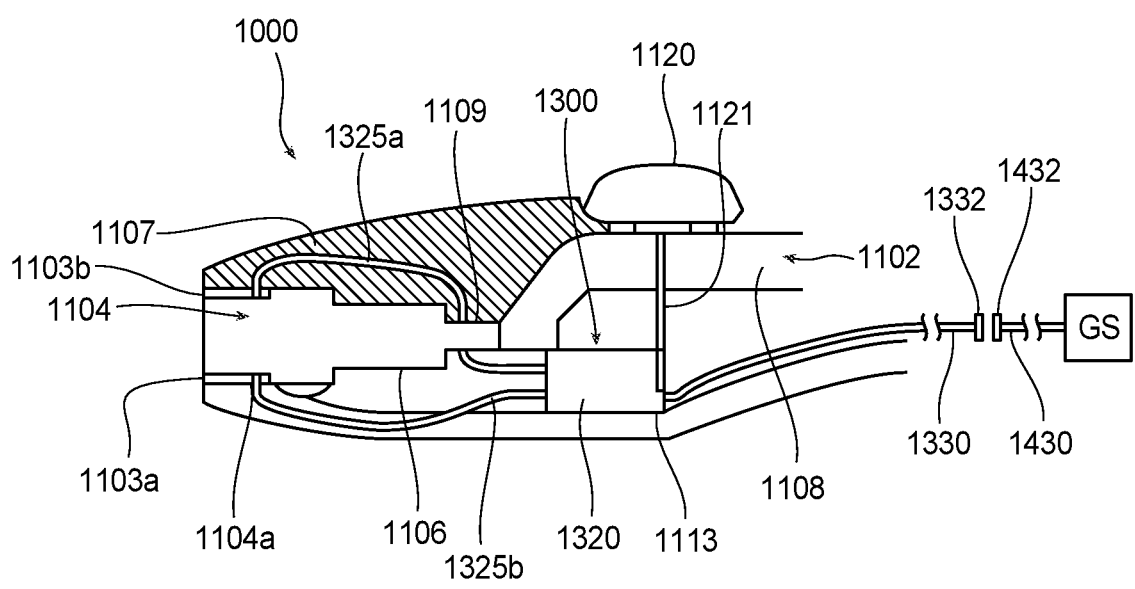
Figure 5D:
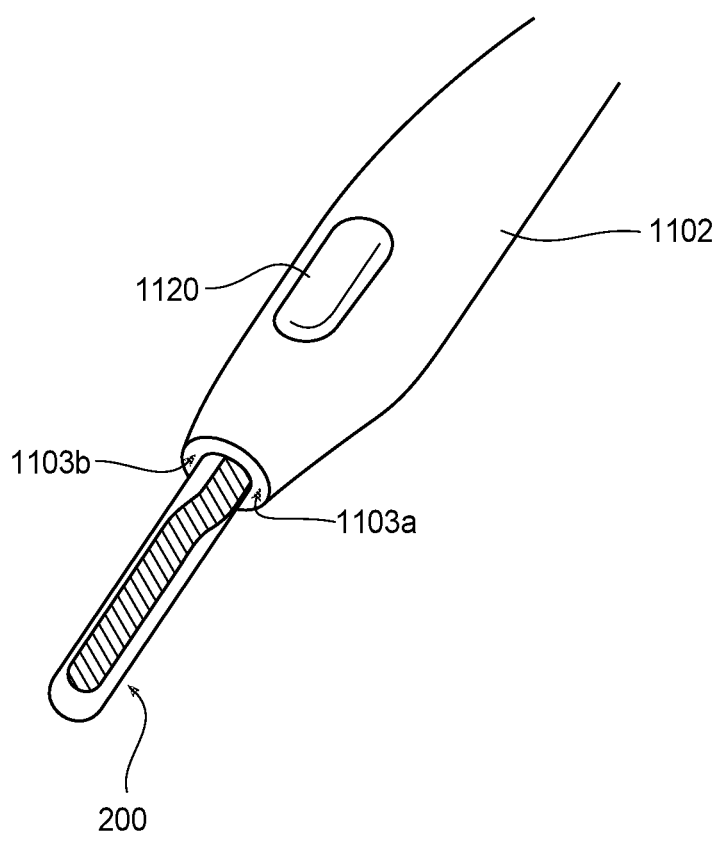
Figure 5E:
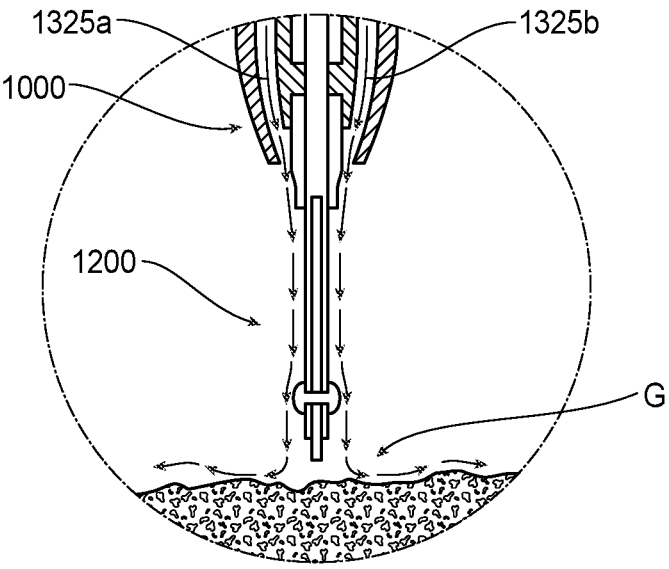
Figure 5F:
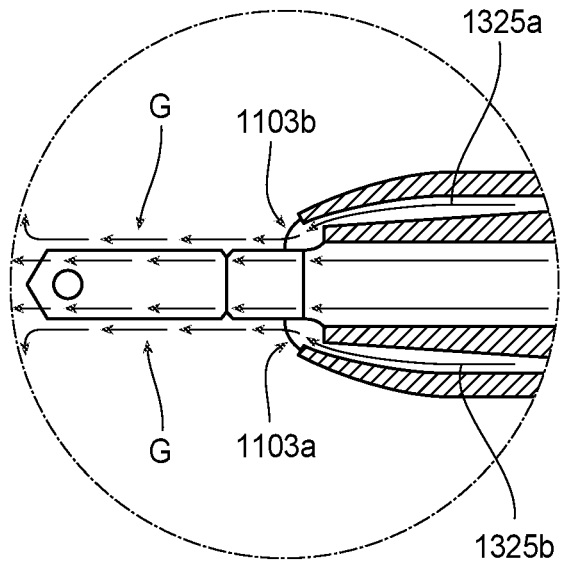

FIG. 4 is a schematic illustration of a voltage divider network for use with the electrosurgical pencil of FIG. 1 and embodiments according to the present disclosure;

FIG. 5A is an enlarged, side view of one embodiment of an end effector assembly according to the present disclosure;

FIG. 5B is an enlarged, sectional view of the end effector assembly of FIG. 5A;

FIG. 5C is an enlarged, sectional view of a distal end of another embodiment of an electrosurgical pencil inclusive of a smoke mitigation assembly for use with the end effector assembly of FIG. 5A;

FIG. 5D is an end, perspective view of the distal end of the electrosurgical pencil of FIG. 5C showing vent holes defined therein and end effector assembly of FIG. 5A shown assembled for use; and FIGS. 5E and 5F are various views of the distal end of the electrosurgical pencil of FIG. 5C illustrating the disbursement of a gas over the end effector assembly of FIG. 5A during activation.

DETAILED DESCRIPTION

Particular embodiments of the presently disclosed electrosurgical pencil configured for bipolar resection are described in detail with reference to the drawing figures wherein like reference numerals identify similar or identical elements. The term "leading edge" refers to the most forward edge with respect to the direction of travel while the term "trailing edge" refers to the edge opposite the leading edge with respect to the direction of travel.

FIG. 1 sets forth a perspective view of an electrosurgical system including a commonly-owned electrosurgical pencil 100 constructed for bipolar resection in accordance with one embodiment of the present disclosure. While the following description is directed towards electrosurgical pencils for bipolar resection, the features and concepts (or portions thereof) of the present disclosure may be applied to any electrosurgical type instrument, e.g., forceps, suction coagulators, vessel sealers, wands, etc. The construction, functionality and operation of electrosurgical pencils, with respect to use for bipolar resection, is described herein. Further details of the electrosurgical pencil are provided in commonly-owned U.S. patent application Ser. No. 16/540, 593 filed Aug. 14, 1019 by Baril et al., the entire contents of which being incorporated by reference herein.

The general functions and elements of the prior art, commonly-owned electrosurgical pencil 100 are discussed herein with reference to FIGS. 1-4 of the above-mentioned prior disclosure U.S. patent application Ser. No. 16/540,593. Electrosurgical pencil 100 includes an elongated housing 102 having a top-half shell portion 102a and a bottom-half shell portion 102b. The elongated housing 102 includes a distal opening 103b, through which a shaft 112 of an end effector assembly 200 extends, and a proximal opening 103a, through which connecting wire 224 (see FIG. 1) extends. Top-half shell portion 102a and bottom-half shell portion 102b may be bonded together using any suitable method, e.g., sonic energy, adhesives, snap-fit assemblies, etc.

Electrosurgical pencil 100 further includes a shaft receptacle 104 disposed at a distal end 103b of housing 102 that is configured to receive the shaft 112 of the selectively removable end effector assembly 200. Electrode assembly 200 is configured to electrically connect to generator "G" through various electrical conductors (not shown) formed in the shaft 112, elongated housing 102, connecting wire 224 and plug assembly 400. Generator "G" may be incorporated into the elongated housing 102 and powered by an internal energy supply, e.g., battery or other energy storage device, fuel cell or other energy generation device or any other suitable portable power source.

Shaft 112 is selectively retained by shaft receptacle 104 disposed in housing 102. Shaft 112 may include a plurality of conductive traces or wires (not shown) along the length of the shaft 112. The conductive traces or wires may be fabricated from a conductive type material, such as, for example, stainless steel, or shaft may be coated with an electrically conductive material. Shaft receptacle 104 is fabricated from electrically conductive materials or includes electrically conductive contacts configured to couple with the plurality of conductive traces or wires of the shaft 112. Shaft receptacle 104 is electrically connected to voltage divider network 127 (FIGS. 2 and 4) as explained in more detail below. Conductive traces or wires of the shaft 112 electrically connect to the electrode assembly 200 as explained in more detail below.

As seen in FIG. 1, electrosurgical pencil 100 may be coupled to a conventional electrosurgical generator "G" via a plug assembly 400 (see FIG. 3), as will be described in greater detail below.

For the purposes herein, the terms "switch" or "switches" includes electrical actuators, mechanical actuators, electro-mechanical actuators (rotatable actuators, pivotable actuators, toggle-like actuators, buttons, etc.) or optical actuators.

Figure 2:
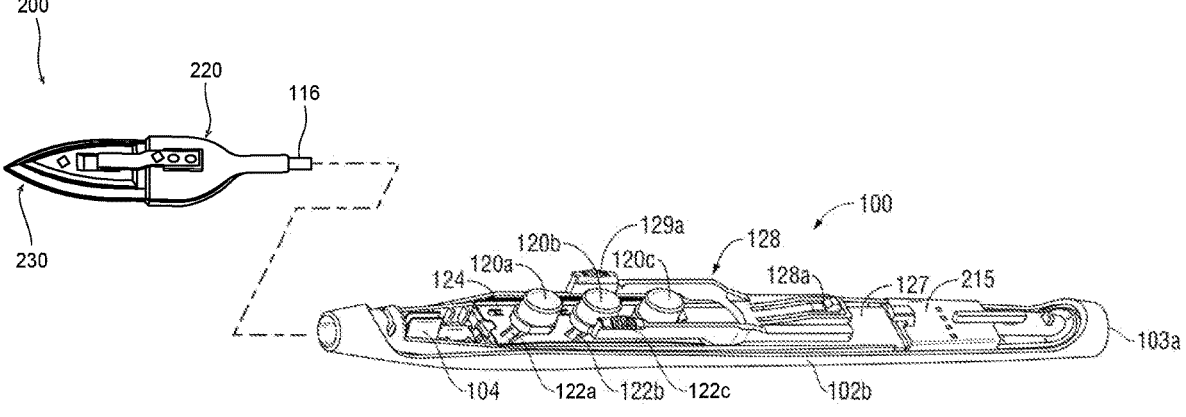
FIG. 2 is a front, top perspective view of the electrosurgical pencil of FIG. 1, with a top-half shell of the housing removed.

Electrosurgical pencil 100 includes one or more activation switches, and may include three activation switches 120a-120c, each of which extends through top-half shell portion 102a of elongated housing 102. Each activation switch 120a-120c is operatively supported on a respective tactile element 122a-122c provided on a switch plate 124, as illustrated in FIG. 2. Each activation switch 120a-120c controls the transmission of RF electrical energy supplied from generator "G" to bipolar electrodes 138 on electrode face 105 of electrode body 112.

More particularly, switch plate 124 is positioned on top of a voltage divider network 127 (hereinafter "VDN 127") such that tactile elements 122a-122c are operatively associated therewith. VDN 127 (e.g., here shown in FIG. 2 as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage. Further details of electrosurgical pencil control are provided in above-mentioned U.S. patent application Ser. No. 16/540,593.

Figure 3:
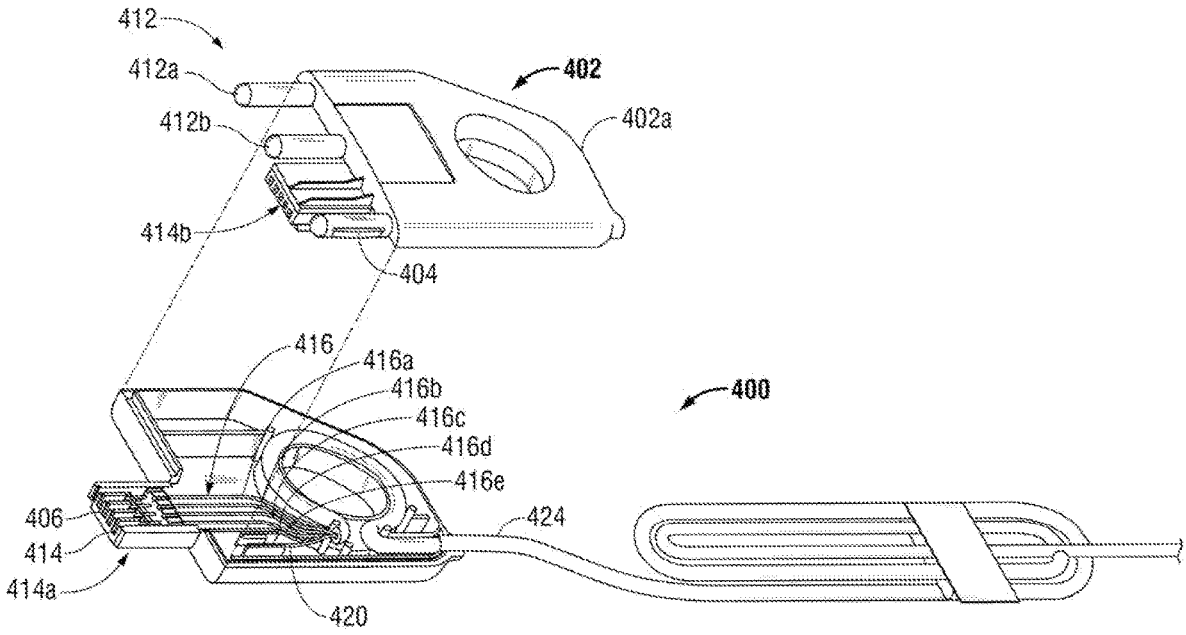
FIG. 3 is a perspective view of the plug assembly of FIG. 1, with a top-half shell section removed therefrom.

In use, depending on which activation switch 120a-120c is depressed a respective tactile element 122a-122c is pressed into contact with VDN 127 and a characteristic signal is transmitted to electrosurgical generator "G" via control wires 416 (see FIG. 3). In one embodiment, three control wires 416a-416c (one for each activation switch 120a-120c, respectively) are provided. Control wires 416a-416c are electrically connected to switches 120a-120c via a control terminal 215 (see FIG. 2) which is operatively connected to VDN 127. By way of example only, electrosurgical generator "G" may be used in conjunction with the device wherein generator "G" includes a circuit for interpreting and responding to the VDN 127 settings.

Activation switches 120a, 120b, 120c are configured and adapted to control the mode and/or "waveform duty cycle" to achieve a desired surgical intent. For example, a first activation switch 120a can be set to deliver a characteristic signal to electrosurgical generator "G" which, in turn, transmits a duty cycle and/or waveform shape that produces a first desirable resection effect. Meanwhile, second activation switch 120b can be set to deliver a characteristic signal to electrosurgical generator "G" which, in turn, transmits a duty cycle and/or waveform shape that produces a second desirable resection effect.

Finally, third activation switch 120c can be set to deliver a characteristic signal to electrosurgical generator "G" which, in turn, transmits a duty cycle and/or waveform shape that produces a third electrosurgical effect/function. Desirable resection effects may include a mode for bipolar coagulation and/or cauterization with an undeployed blade, a mode for bipolar resection with a partially deployed blade, a mode for bipolar resection with a fully deployed blade, a mode for monopolar resection and a mode for resection with blended energy delivery (monopolar and bipolar modes), as will be described in greater detail hereinbelow.

As seen in FIG. 3, fourth and fifth wires (e.g., first RF line 416d and second RF line 416e) are provided and electrically connect to respective active and return electrodes 239, 234 of the end effector assembly 200 (See FIG. 1). Since first RF line 416d and second RF line 416e are directly connected to the end effector assembly 200, first RF line 416d and second RF line 416e bypass the VDN 127 and are isolated from VDN 127 and control wires 416a-416c. By directly connecting the first RF line 416d and second RF line 416e to the end effector assembly 200 (as explained in more detail below) and isolating the VDN 127 from the RF energy transmission, the electrosurgical current does not flow through VDN 127. This, in turn, increases the longevity and life of VDN 127 and/or activation switches 120a, 120b, 120c.

With reference to FIG. 4, VDN 127 is shown and includes a first transmission line 127a configured to operate the various modes of electrosurgical pencil 100; a second transmission line 127b configured to operate the various intensities of electrosurgical pencil 100; a third transmission line 127c configured to function as a ground for VDN 127; and a fourth transmission line 127d which transmits up to about +5 volts to VDN 127.

First RF line 416d and second RF line 416e are isolated from or otherwise completely separate from VDN 127. In particular, first RF line 416d and second RF line 416e extends directly from the RF input or generator "G" to the active electrode 239 and return electrodes 234a, 234b of the end effector assembly 200 as explained in more detail below.

By way of example only, VDN 127 may include a plurality of resistors "R1" (e.g., six resistors), connected in a first series between third transmission line 127c and fourth transmission line 127d. The first series of resistors "R1" may combine to total about 1000 ohms of resistance. The first series of resistors "R1" are each separated by a first set of switches "S1". Each switch of the first set of switches "S1" may be electrically connected between adjacent resistors "R1" and first transmission line 127a of VDN 127. In operation, depending on which switch or switches of the first set of switches "S1" is/are closed, a different mode of operation for electrosurgical pencil 100 is activated.

Resection may be performed with electrosurgical energy including waveforms having a duty cycle from about 10% to about 100%. The dual effect of coagulating and cauterizing, as described herein, may be performed with a waveform having a duty cycle from about 10% to about 100%. To increase the depth of coagulation may require a waveform with a duty cycle from about 50% to 100%. It is important to note that these percentages are approximated and may be customized to deliver the desired surgical effect for various tissue types and characteristics.

In one embodiment, the waveforms provided to the bipolar electrosurgical pencil 100 may be dynamically controlled by the generator "G". For example, the mode of operation provided by switches S1, S2, S3 may indicate a range of operation for the generator "G". Generator "G" provides a waveform within the specified range of operation wherein the waveform is dynamically changed based on a parameter, wherein the parameter may be related to one of energy delivery, the target tissue and the duration of energy delivery. The parameter may be obtained from a source external to the generator "G", such as, a measured parameter or clinician provided parameter, or the parameter may include an internal parameter obtained, measured or determined by the generator "G".

As seen throughout FIG. 2, electrosurgical pencil 100 further includes an intensity controller 128 slidingly supported on or in elongated housing 102. Intensity controller 128 may be configured to function as a slide potentiometer, sliding over and along VDN 127 wherein the distal-most position corresponds to a relative high intensity setting, the proximal-most position corresponds to a low intensity settings with a plurality of intermediate positions therebetween. As can be appreciated, the intensity settings from the proximal end to the distal end may be reversed, e.g., high to low.

The intensity settings are typically preset and selected from a look-up table based on a choice of electrosurgical instruments/attachments, desired surgical effect, surgical specialty and/or surgeon preference, the type of end effector assembly 200 and the arrangement of the active and return electrodes 239, 234. The selection of the end effector assembly 200, the intensity setting and duty cycle determines the surgical effect. The settings may be selected manually by the user or automatically. For example, the electrosurgical generator "G" may automatically determine the type of end effector assembly 200 and a predetermined intensity value may be selected and subsequently adjusted by the user or the electrosurgical generator "G".

Turning now to FIG. 3, a detailed discussion of plug assembly 400 is provided. Plug assembly 400 includes a housing portion 402 and a connecting wire 424 that electrically interconnects the housing portion 402 and the control terminal 215 in the electrosurgical pencil 100 (see FIG. 2). Housing portion 402 includes a first half-section 402a and a second half-section 402b operatively engageable with one another, e.g., via a snap-fit engagement. First half-section 402a and second half-section 402b are configured and adapted to retain a common power pin 404 and a plurality of electrical contacts 406 therebetween.

Common power pin 404 of plug assembly 400 extends distally from housing portion 402 at a location between first half-section 402a and second half-section 402b. Common power pin 404 may be positioned to be off center, i.e., closer to one side edge of housing portion 402 than the other. Plug assembly 400 further includes at least one a pair of position pins 412 also extending from housing portion 402. Position pins 412 may be positioned between the first half-section 402a and the second half-section 402b of housing portion 402 and are oriented in the same direction as common power pin 404.

A first position pin 412a is positioned in close proximity to a center of housing portion 402 and a second position pin

412b is positioned to be off center and in close proximity to an opposite side edge of housing portion 402 as compared to common power pin 404. First position pin 412a, second position pin 412b and common power pin 404 may be located on housing portion 402 at locations which correspond to pin receiving positions (not shown) of a connector receptacle "R" of electrosurgical generator "G" (see FIG. 1).

Plug assembly 400 further includes a prong 414 extending from housing portion 402. In particular, prong 414 includes a body portion 414a extending from second half-section 402b of housing portion 402 and a cover portion 414b extending from first half-section 402a of housing portion 402. In this manner, when the first half-section 402a and the second half-section 402b are joined to one another, cover portion 414b of prong 414 encloses the body portion 414a. Prong 414 may be positioned between common power pin 404 and first position pin 412a. Prong 414 is configured and adapted to retain electrical contacts 406 therein such that a portion of each electrical contact 406 is exposed along a front or distal edge thereof. While five electrical contacts 406 are shown, any number of electrical contacts 406 can be provided, including and not limited to two, six and eight. Prong 414 may be located on housing portion 402 at a location that corresponds to a prong receiving position (not shown) of connector receptacle "R" of electrosurgical generator "G" (see FIG. 1).

Since prong 414 extends from second half-section 402b of housing portion 402, housing portion 402 of plug assembly 400 will not enter connector receptacle "R" of electrosurgical generator "G" unless housing portion 402 is in a proper orientation. In other words, prong 414 functions as a polarization member. This ensures that common power pin 404 is properly received in connector receptacle "R" of electrosurgical generator "G".

Connecting wire 424 includes a power supplying wire 420 electrically connected to common power pin 404, control wires 416a-416c electrically connected to a respective electrical contact 406, and first RF line 416d and second RF line 416e electrically connected to a respective electrical contact 406.

Turning to FIG. 5A-5F, the presently disclosed end effector assembly 1200 may be used with an electrosurgical pencil 1000 and includes a shaft 1212 having a proximal portion 1214 configured to mechanically and electrically engage shaft receptacle 1104 (See FIG. 5C). Shaft 1212 and shaft receptacle 1104 are configured to provide a plurality of suitable electrical connections therebetween to facility the delivery of electrosurgical energy from the electrosurgical generator "G" (See FIG. 1) to an active electrode 1225 and return or ground electrode 1217.

A proximal or active pin 1214 of shaft 1212 is inserted into distal opening 1103 of the elongated housing 1102 to engage shaft receptacle 1104. Shaft receptacle 1104 is configured to mechanically and electrically couple the shaft 1212 to the elongated housing 1102. Electrical connections may include one or more electrical connectors 1109, 1108 (or electrical connector pairs) that connect to the active electrode or active pin 1214 and one or more electrical connectors or conductive rings 1104a that connect to the ground electrode 1217 and ground wire 1113 upon engagement of the shaft 1212 into shaft receptacle 1104. Shaft 1212 and shaft receptacle 1104 may include a locking device, such as, for example, a shaft locking pin that slides into and engages a shaft locking pin receptacle (not explicitly shown). Any suitable securing and/or locking apparatus may be used to releasably secure the shaft 1212 to the elongated housing 1102. As described herein, the shaft 1212 is interchangeable within a distal end 1107 of the elongated housing 1102. In other embodiments, shaft 1212 is integrated into the elongated housing 1102 and is not replaceable.

Turning back to FIGS. 5A and 5B, electrode assembly 1200 includes an insulative support 1240, e.g., a ceramic core, configured to support an active electrode or active wire 1225, e.g., a tungsten wire, around a peripheral surface thereof. The wire 1225 may be crimped or otherwise secured to the ceramic core 1240. Wire 1225 electrically couples to active pin 1214 which, in turn, electrically couples to contact 1108 disposed in housing 1102. A ring-like ground connection 1217 is disposed about the proximal end of the electrode assembly 1200 for connection to a corresponding connector 1104*a* disposed in distal opening 1103 upon engagement of the end effector assembly 1200 with the housing 1102 for ultimate connection to ground wire 1113. Shaft receptacle 1104 may include one or more mechanical interfaces, e.g., step-like surfaces 1106, to facilitate engagement of the end effector 1200 with housing 1102. Contact 1108, in turn, operably couples to one or more switches 1120 (See FIG. 5C) disposed on housing 1102 used to activate the generator "G" to energize the electrodes 1225 and 1217 in a bipolar manner. The variously described switches 120*a*-120*c* with respect to FIGS. 1-4 may also be utilized along with the intensity controllers 129*a*, 129*b* associated therewith.

Turning back to FIGS. 5A and 5B, electrode assembly 1200 includes an insulative plastic 1221 disposed between the ground electrode 1217 and the active wire 1225 configured to insulate the two electrodes 1225, 1217 during activation. A hollow tube or hypotube 1219 encapsulates a portion of the active wire 1225 and further insulates the active wire 1225 from the ground electrode 1217. Hypotube 1219 is also configured to mechanically engage step area 1106 of shaft receptacle 1104 to facilitate secure engagement of the end effector assembly 1200 therein (See FIG. 5C).

By providing a single pole (or active wire 1225) connection to the activation contact 1108 coupled with an in-line connection to the ground electrode 1217, the overall profile of the pencil 1000 is significantly reduced compared to a two-pole configuration providing greater visibility to the surgical site.

FIG. 5C shows an internal view of a smoke mitigation assembly (SMA) 1300 operably disposed within the electrosurgical pencil 1000 for use with end effector assembly 1200. SMA 1300 is disposed within the housing 1102 and may be integrally coupled thereto or may be configured as an auxiliary internal or external (not shown) attachment. As shown, the SMA is integrally associated within the pencil 1000.

SMA includes an air control valve 1320 that operably couples to activation switch 1120 such that, upon actuation, a gas "G" e.g., CO2, may be dispersed atop end effector 1200 simultaneously with bipolar activation of the pencil 1000. Alternatively, the switch 1120 may be configured as a two-stage or multi-stage switch such that the gas "G" may be dispersed in a first stage prior to bipolar activation. The gas "G" may also be delivered in the second stage after bipolar activation. The gas "G" may also be delivered with a multi-stage switch; a first stage at a low flow rate and one or more subsequent stages at a higher flow rate. Moreover, the gas "G" may be delivered in varying stages prior to and after bipolar activation; a first stage with a low flow prior to bipolar activation and a second stage with a higher flow after activation (if needed to further reduce smoke or to provide a quick burst to clear the operating site). The transition from the first stage through the multiple stages of the activation switch 1120 is through the range of motion of the activation switch 1120.

Control valve 1320 regulates the flow of gas "G" from a gas source GS to a one or more vents 1103*a*, 1103*b* defined at the distal end 1103 of pencil 1000. More particularly, a gas tube 1430 extends from the gas source GS and is configured to include a luer-type connector 1432 that operably connects to a complementary luer-like interface 1332 operably associated with a second tube 1330 that extends through the housing 1102. Second tube 1330 connects to the air control valve 1320. Upon activation of the switch 1120 in one of the manners described above, gas "G" is supplied under pressure to one or more dispersion tubes, e.g., dispersion tubes 1325*a*, 1325*b*, that operably connect the air control valve 1320 to the vents 1103*a*, 1103*b* defined at the distal end 1103 of the pencil 1000. Vents 1103*a*, 1103*b* direct the gas "G" over the end effector 1200 on either side thereof (e.g., along the surface area of the end effector assembly 1200) towards the distal end of the end effector assembly 1200, essentially bathing the entire end effector assembly 1200 in gas "G" (See FIGS. 5E and 5F). Although only vents 1103*a*, 1103*b* are shown and described, more or less vents may be utilized. The vents 1103*a*, 1103*b* may include geometry to control the direction of the gas "G" towards the surface of the end effector assembly 1200.

Although CO2 gas is described herein, various other gases may be utilized to accomplish the same or similar purposes, e.g., air, other inert gases, etc. Moreover and as mentioned above, the flow rate of the gas "G" may be controlled by the switch 1120 or, in some instance, may be controlled at the gas source GS or by a regulation device (not shown) associated with the gas source GS, tubing 1430, 1330 or air control valve 1320. Alternatively, a gas cylinder or cartridge (not shown) may be disposed within the housing 1102 and act as the gas supply GS. In embodiments, a separate gas switch (not shown) may be operably associated with the housing 1102 or provided as an external switch (e.g., footswitch, gas supply GS switch) utilized to accomplish the same or similar purpose. Moreover, a gas "kill" switch (not shown) may be operably associated with the housing 1102 or gas source GS which would allow bipolar activation without gas "G" disbursement.

During use, the gas "G" is released such that the end effector assembly 1200 is essentially bathed with the gas "G" which may limit sparkling at or near the tissue site thereby reducing or mitigating the amount of smoke generated during cutting. By eliminating the smoke, the surgeon has a clearer view of the operating site.

Although shown and described with a bipolar electrosurgical pencil, it is contemplated that a monopolar electrosurgical pencil may be configured to house or operably couple to the above-described or similar smoke mitigation assembly 1300.

In embodiments, the housing 1102 may include internal geometry and an array of seals defined therein that are configured to replace one or more of tubes 1330, 1325*a*, 1325*b*.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. For example, the knife body and tube do not necessarily have to be made from the exact same materials. Similar materials, or any two materials that can be welded together to allow for a durable weld joint could be used.

What is claimed is:

1. An electrosurgical pencil, comprising:
a housing configured to be coupled to an end effector assembly;
a multi-stage activation switch operably disposed on the housing and configured to cause delivery of electrosurgical energy to the end effector assembly upon transition of the multi-stage switch to a first stage; and
an air control valve in communication with the multi-stage activation switch and configured to control a flow of gas toward the end effector assembly, wherein transition of the multi-stage switch to a second stage is configured to cause simultaneous delivery of the gas and the electrosurgical energy to the end effector assembly.

2. The electrosurgical pencil according to claim 1, wherein the housing includes at least one vent configured to direct the gas toward the end effector assembly.

3. The electrosurgical pencil according to claim 2, further comprising a dispersion tube fluidly coupling the air control valve to the at least one vent.

4. The electrosurgical pencil according to claim 2, wherein the at least one vent comprises a plurality of vents defined about a distal end portion of the housing and configured to direct the gas toward the end effector assembly.

5. The electrosurgical pencil according to claim 1, wherein the gas is carbon dioxide.

6. The electrosurgical pencil according to claim 1, wherein transition to one stage of the multi-stage activation switch causes delivery of the gas to the end effector assembly at a first flow rate and transition to another stage of the multi-stage activation switch causes delivery of the gas to the end effector assembly at a second flow rate different than the first flow rate.

7. The electrosurgical pencil according to claim 1, wherein the multi-stage activation switch includes a third stage for causing delivery of the gas to the end effector assembly.

8. An electrosurgical device, comprising:
a housing;
an end effector assembly; and
an activation switch operably disposed on the housing and configured to cause delivery of electrosurgical energy to the end effector assembly, the activation switch configured to communicate with an air control valve disposed within the housing to control delivery of a gas to the end effector assembly, the activation switch including a first stage for causing the delivery of the electrosurgical energy to the end effector assembly and a second stage for causing the delivery of the gas and the electrosurgical energy to the end effector assembly.

9. The electrosurgical device according to claim 8, wherein the housing includes at least one vent configured to direct the gas toward the end effector assembly.

10. The electrosurgical device according to claim 9, further comprising a dispersion tube fluidly coupling the air control valve to the at least one vent.

11. The electrosurgical device according to claim 9, wherein the at least one vent comprises a plurality of vents defined about a distal end portion of the housing and configured to direct the gas toward the end effector assembly.

12. The electrosurgical device according to claim 8, wherein the gas is carbon dioxide.

13. The electrosurgical device according to claim 8, wherein transition to one stage of the activation switch causes delivery of the gas to the end effector assembly at a first flow rate and transition to another stage of the activation switch causes delivery of the gas to the end effector assembly at a second flow rate different than the first flow rate.

14. The electrosurgical device according to claim 8, wherein the activation switch includes a third stage for causing delivery of the gas to the end effector assembly.

15. An electrosurgical smoke mitigation device, comprising:

a housing;

an end effector assembly configured to receive electrosurgical energy from an electrosurgical energy source for treating tissue;

an air control valve disposed within the housing and configured to control a flow of a gas to at least one vent disposed at a distal end portion of the housing, the at least one vent configured to direct the flow of the gas from the distal end portion of the housing toward the end effector assembly for mitigating smoke at a surgical site, wherein the air control valve is configured to cause the gas to flow at a first flow rate and at a second flow rate different than the first flow rate; and an activation switch disposed on the housing and configured to control delivery of the electrosurgical energy to the end effector assembly.

16. The electrosurgical smoke mitigation device according to claim 15, wherein the activation switch includes multiple stages for controlling delivery of the electrosurgical energy to the end effector assembly and the flow of the gas to the at least one vent.

17. The electrosurgical smoke mitigation device according to claim 16, wherein transition to one stage of the activation switch causes the gas to flow at the first flow rate and transition to another stage of the activation switch causes the gas to flow at the second flow rate.

18. The electrosurgical smoke mitigation device according to claim 15, wherein the gas is carbon dioxide.

19. The electrosurgical smoke mitigation device according to claim 15, further comprising a dispersion tube fluidly coupling the air control valve to the at least one vent.

20. The electrosurgical smoke mitigation device according to claim 15, wherein the at least one vent comprises a plurality of vents defined about a distal end portion of the housing and configured to direct the gas toward the end effector assembly.

* * * * *